United States Patent [19]

Meng et al.

[11] Patent Number: 4,842,998
[45] Date of Patent: Jun. 27, 1989

[54] HETEROHYBRIDOMA SCREENING METHOD

[75] Inventors: Y. Gloria Meng, Albany; Jurgen Trawinski, El Sobrante, both of Calif.

[73] Assignee: Miles Inc., Elkhart, Ind.

[21] Appl. No.: 120,047

[22] Filed: Nov. 9, 1987

[51] Int. Cl.$^4$ ............................................. G01N 33/77
[52] U.S. Cl. ...................................... 435/7; 435/172.2; 435/172.3; 435/68; 435/240.27; 530/387; 436/540; 436/513; 436/512; 436/547; 935/92; 935/96; 935/100; 935/104
[58] Field of Search ............. 435/68, 172.2, 7, 240.27; 436/540, 513, 512, 547; 935/92, 96, 100, 104; 530/387

[56] References Cited

PUBLICATIONS

Kobayashi, K. et al. "Improved Procedure for the Isolation of J-chain from Human Polymeric Immunoglobulins," *Biochim. Biophys. Acta.* 303:105-117, 1973.
Herbert, W. J. et al. (eds.), *Dictionary of Immunology*, Blackwell Scientific Publications, Oxford, 1985, pp. 110 and 148.
Kuo, M. et al. "Rabbit-Mouse Hybridomas Secreting Intact Rabbit Immunoglobulin," *Molecular Immunology* 22(4):351-359, 1985.
Goding, J. W., *Monoclonal Antibodies:Principles and Practice*, Academic Press, Inc., Orlando, Fla., 1983, pp. 175-178.

*Primary Examiner*—Margaret Moskowitz
*Assistant Examiner*—Kay E. Cheney
*Attorney, Agent, or Firm*—James A. Giblin

[57] ABSTRACT

Human-nonhuman heterohybridomas capable of expressing IgM type antibodies can be screened to select hybridomas expressing IgM antibodies comprising human J chain components. Method comprises contacting separate samples of IgM antibodies (or IgM J chain components) from a given cell line with anti-human J chain antibodies and anti-non-human J chain antibodies to determine which antibody complexes with the J chain component of the samples, thereby identifying and permitting the early selection of a heterohybridoma expressing IgM having a human J chain component.

14 Claims, 2 Drawing Sheets

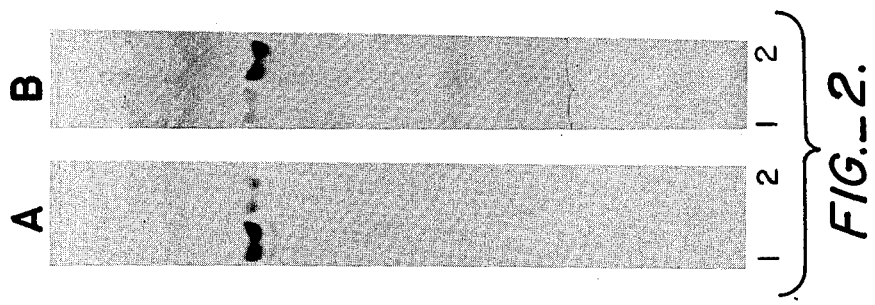
FIG._2.
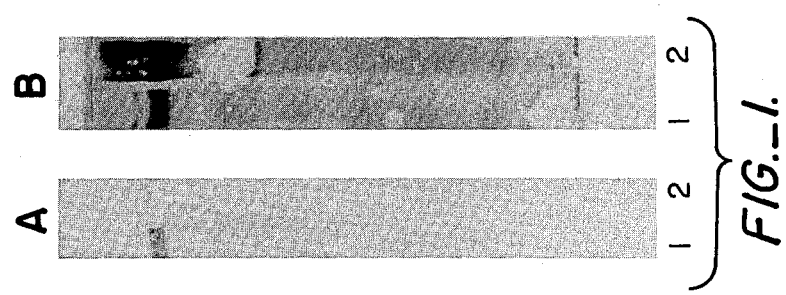
FIG._1.

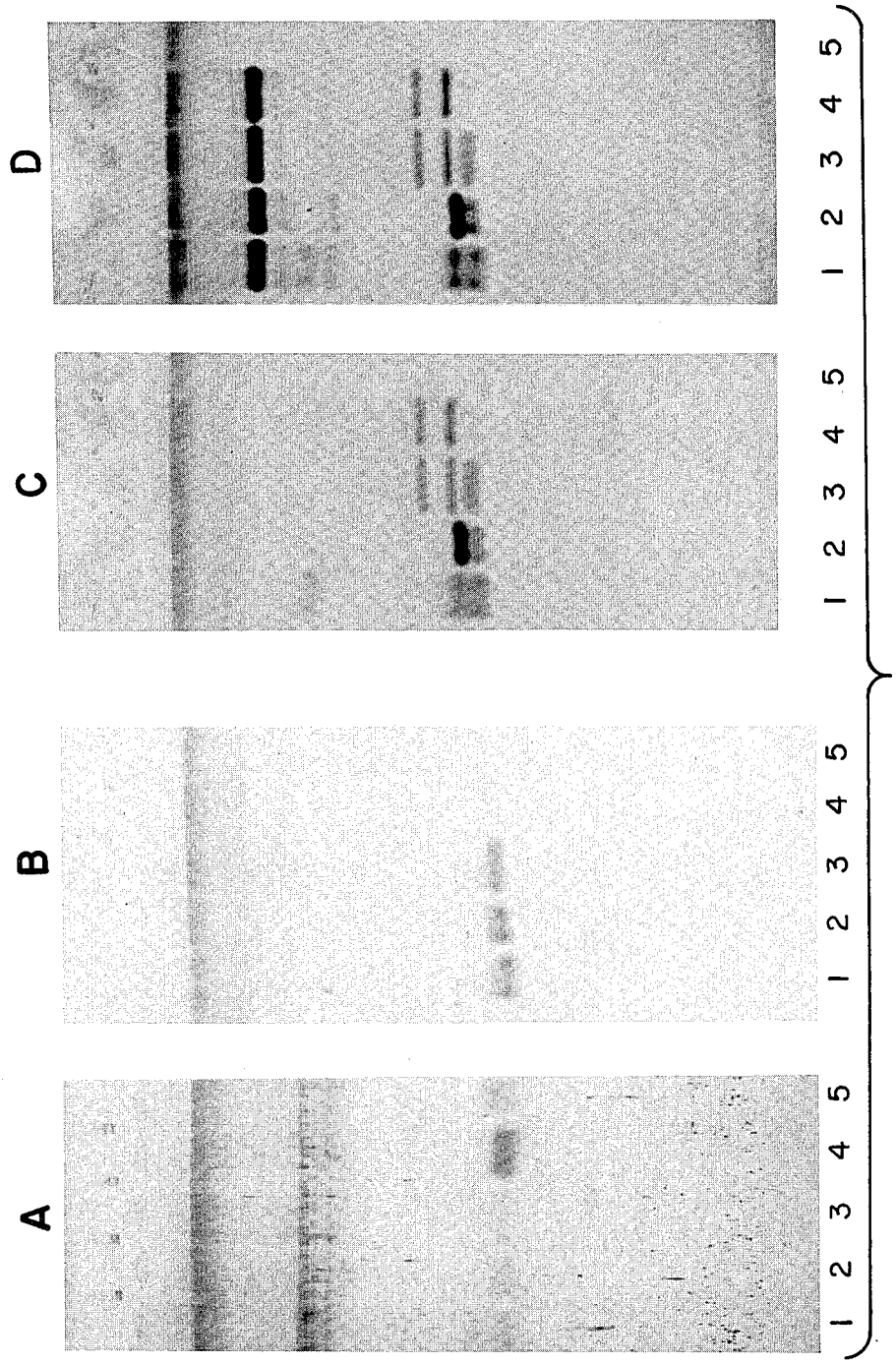

HETEROHYBRIDOMA SCREENING METHOD

BACKGROUND OF THE INVENTION

1. Field:

This disclosure is concerned generally with the production of monopclonal antibodies and specifically with a technique for the selection of desirable cell lines from a collection of human-nonhuman hybridoma cells capable of expressing monoclonal antibodies of the IgM type.

2. Prior Art:

It is well known that antibodies in general can be classified according to a standard typing scheme (i.e. $IgG_1$, $IgG_2$, $IgG_3$, $IgG_4$, IgM, IgE, and IgA). This disclosure is especially concerned with antibodies of the IgM type.

IgM is a well known 19S immunoglobulin which comprises about 7% of the immunoglobulins found in humans. IgM antibodies have so-called J chain, light chain, and heavy chain components and are said to have an antibody valence of at least five. They are the earliest antibodies generated in an immune response. IgM antibodies tend to be very effective, especially in combating bacterial infections. They can be obtained from human plasma using known plasma fractionation techniques (e.g. U.S. Pat. No. 4,318,902 to Stephan).

The production of monoclonal antibodies, including the IgM type, has become well known since the early article by Kohler and Milstein, "Continuous Cultures of Fused Cells Secreting Antibody of Predefined Specificity", Nature 256:495-497 (1975). Those antibodies can now be made in various ways such as using somatic cell hybrids (see, for example, U.S. Pat.. No. 4,172,124 to H. Koprowski et al.) or transformed cells (see, for example, U.S. Pat. No. 4,446,465 to M. Lostrom).

Purified monoclonal IgM preparations are described by D. Nau, Biochromatography, 1, No. 2, pp. 83-84 (95% pure IgM from tissue culture); M. Flashner, U.S. Pat. No. 4,604,235 (90% pure IgM from mouse ascites fluid and which was characterized as "essentially pure antibody"); J. R. Wands et al., W 082/01072 (high affinity IgM monoclonal antibodies for diagnostics, cited above); and T. Brooks et al., Amer. Lab., October, 1985 (use of hydroxylapatite for purification of mouse and human IgG and IgM).

It is well known that fusion with mouse cell lines is a common way to improve certain cell line properties. When a cell line producing human IgM is fused with a mouse cell line, mouse J chain may be incorporated in the IgM. When IgM monoclonals are expressed by such heterohydbridoma cell lines, especially if intended for therapeutic use where immunological reactions are to be avoided, it is highly desirable to develop only those cell lines expressing IgM that consists of human components for the J chain of the IgM molecule. Unfortunately, when a given IgM expressing heterohybridoma is first made (e.g., by fusion of a mouse myeloma cell and a EBV transformed human cell line), there is no practical way to assure that both the J chain and light chain components of the expressed IgM will be of or correspond to those of human origin. Whether a given cell line will express IgM having desired human components is essentially a matter of chance. Hence, it would be highly desirable to have a method available for the early screening of heterohybridoma cell lines for only human IgM components.

Quite surprisingly, we have now found that this can be done by a relatively simple technique that can be used at an early stage of cell line selection. The technique can be used with crude IgM preparations or, with non-reduced or, preferably, with reduced and further purified preparations. Clones producing desirable IgM can now be detected early in the cloning procedure, thus saving considerable time and labor. This helps avoid the costly development of undesirable cell lines so that one can focus only on those cell lines desired. Details of our methods are described below.

SUMMARY OF THE INVENTION

As used herein, the term desirable cell, desirable cell line, or desirable clone means a human-non-human heterohybridoma which expresses IgM antibodies having a human J chain component.

Our method of selecting desirable cells from a collection of human-nonhuman heterohybridoma cells capable of expressing IgM type antibodies comprises three major steps: (1) The collection and processing of the IgM antibodies to expose J chain components; (2) the exposure of separate samples of the antibodies to anti-human and anti-non-human J chain antibodies; and (3) the determination of which are reactive with the sample IgM antibodies. The determination of step (3) can be accomplished, for example, with labelled labels are well known to those skilled in the art (e.g. conjugated enzymes, etc.)

In a preferred embodiment, samples of a crude tissue culture supernatant containing crude IgM antibodies from each of the heterohybridomas are collected. The crude IgM antibodies are then denatured [e.g., by sodium dodecyl sulfate (SDS)] and subjected to electrophoresis (e.g., loaded on a SDS gel containing low percentage of acrylamide and agarose). Albumin, which exists in huge quantity in the supernatant, moves toward the bottom of the electrophoresis gel in the above gel system and IgM stays on top of the gel and good IgM bands can be obtained. Protein blots of this gel in duplicates are then probed with either anti-human J chain or anti-mouse J chain antibody. This general method is useful for initial screening.

Later, in a more preferred confirmatory embodiment, the relatively crude IgM samples can be purified by an affinity column or other methods and run on the same gel. Or, more preferably, purified samples of IgM are subjected to reducing conditions (by e.g. $\beta$-mercaptoethanol or dithiothreitol) in addition to denaturing conditions (by SDS) and run on 15% actrylamide SDS gel which separates heavy chain, light chain and J chain. Protein blots in duplicates are then probed with anti-mouse or anti-human J chain antibody. This later gel has good separation and provides a good way to confirm the initial screening results to assure that the hybridoma IgM does not contain mouse J chain.

We have found the test can be done with culture fluid comprising as little as about 30 $\mu$g of IgM antibody per ml of fluid (although concentrations even as low as 5 $\mu$g/ml can be used after a suitable concentrations step).

BRIEF DESCRIPTION OF THE FIGURES

FIG. 1 illustrates a blot comparing probes wtih both anti-mouse and anti-human J chain antibodies on relatively crude, non-reduced IgM samples expressed from a mouse-human heterohybridoma.

FIG. 2 illustrates a bolt comparing similar probes on purified, non-reduced IgM samples.

FIG. 3a, 3b, 3c and 3d illustrate blots comparing similar probes on reduced and purified IgM samples.

DETAILED DESCRIPTION

Our methods are illustrated in the Examples given below. In the first Example a relatively crude and non-reduced IgM source was tested. In the second and third Examples, purified and purified and reduced samples of IgM, respectively, were tested. The differences in results are illustrated in the Figures.

Materials and Methods: For the results obtained in our Examples, the IgM expressing cell line was designated 9D10, A.T.C.C. accession No. CRL 8752. The IgM was specific to Fisher 4, Psuedomonas aeruginosa antigen. The detergent used in the denaturation step was sodium dodecyl sulfate.

EXAMPLE I (From Crude IgM)

About 0.8 ml of tissue culture supernatant from IgM producing clones were mixed with 0.02 ml of loading mixture containing 4% SDS and loaded onto 2.5% acrylamide, 0.5% agarose gel. The J chain components were exposed under such conditions. The gel was blotted onto nitrocellulose paper and separate samples of the IgM preparations were probed with anti-mouse J chain and anti-human J chain antibodies. Labeled secondary antibody was then used for visualizing protein bands. Clones secreting IgM with mouse J chain showed a darker band when probed with mouse J chain antibody than when probed with anti-human J chain antibody. The results of this technique can be seen in FIG. 1. Unreduced tissue culture supernatant of the 9D10 cell line (sample 1) and 9D10/X63 cell line, a fusion derivative of the human cell line 9D10 and the mouse cell line X63-Ag8.653 (sample 2), were run on a 2.5% acrylamide and 0.5% agarose SDS gel in duplicates and were blotted onto nitrocellulose paper. One blot was probed with rabbit anti-human J chain antibody (blot A), the other with goat anti-mouse J chain antiserum (blot B). Peroxidase labelled anti-rabbit and anti-goat antibody were used respectively to visualize bands using 4-C1-1-naphthol as the substrate. Sample 1 contained about 33 µg/ml of the 9D10 IgM. Sample 2 originally contained 5 µg/ml of 9D10/X63 IgM and was concentrated 8-fold by a Centricon filtering device (Amicon). In FIG. 1 it can be seen that the 9D10/X63 tissue culture supernatant gave a darker band than 9D10 tissue culture supernatant when probed with anti-mouse J chain antiserum and a much lighter band than the 9D10 tissue culture supernatant when probed with anti-human J chain antibody. This indicates an IgM having undesirable mouse J chain. The clone expressing this antibody can thus be eliminated from further development.

EXAMPLE II (Non-reduced and Purified IgM)

Purified IgM (see below) was used instead of crude IgM. The results of ths technique are shown in FIG. 2. About 0.005 A280 units of purified, unreduced 9D10 IgM (sample 1) and 9D10/X63 IgM (sample 2) were run on agarose acrylamide gel and blotted and probed as in FIG. 1. Blot A was probed with anti-human J chain antibody and blot B with anti-mouse J chain antiserum as in FIG. 1. The 9D10 IgM and 9D10/X63 IgM were affinity purified by using a monoclonal anti-IgM column. The 9D10 IgM and 9D10/X63 IgM have the same LPS binding activity by ELISA (data not shown). Again, the 9D10/X63 IgM gave a darker band when probed with anti-mouse J chain antibody.

EXAMPLES III (reduced and Purified IgM)

Early screening results can be confirmed, if desired, by using reduced and purified IgM. The results of using these techniques are shown in FIG. 3. About 5 µg of purified IgM samples in 1% SDS were reduced with β-mercaptoethanol and were run on a 15% SDS acrylamide gel in duplicates and were blottted onto nitrocellulose paper. Samples were affinity purified plasma IgM (lane 1), human monoclonal IgM against Fisher type 2 Pseudomonas aeruginosa LPS (lane 2), 9D10 IgM (lane 3), 9D10/X63 IgM (lane 4) and mouse monoclonal IgM (produced from a hybrid of MPC 11 and WEHI 231, lane 5). One blot was probed with anti-mouse J chain antiserum (blot A) and the other with anti-human J chain antibody (blot B) as in FIG. 1. Blot B was further probed with peroxidose labelled anti-human IgG (H+L) antibody (blot C), followed by peroxidase labelled anti-human µ chain antibody (blot D). Heavy chain, light chain and J chain are labelled as H, L and J. 9D10 IgM and 9D10/X63 IgM both have an additional glycosylated light chain and showed two light chain bands on the blot.

Given the above disclosure, it is thought that variations will now occur to those skilled in the art. Accordingly, it is intended that the above example should be construed as illustrative here should be limited only by the following claims.

We claim:

1. A method of selecting a human-nonhuman heterohybridoma which expresses IgM antibodies having a human J chain component from a collection of human-nonhuman heterohybridoma clones capable of expressing human IgM type antibodies, the method comprising the steps of
    (a) collecting tissue culture fluid containing samples of IgM antibodies from each of the heterohybridomas and treating the antibodies under conditions sufficient to expose the J chain components of the antibodies;
    (b) separately contacting the samples of IgM antibodies to anti-human J chain antibodies and anti-nonhuman J chain antibodies capable of complexing with the nonhuman J chain components of IgM antibodies;
    (c) determining which of the antibodies of step (b) complexes with the IgM antibodies; and
    (d) selecting those heterohybridomas which produced IgM antibodies which bind to anti-human J chain antibodies.

2. The method of claim 1 wherein the heterohybridoma clones are mouse-human cells.

3. The method of claim 1 wherein the detergent is used to expose the J chain component in step (a).

4. The method of claim 3 wherein the exposure includes use of SDS.

5. A method of selecting a human-nonhuman heterohybridoma which expresses IgM antibodies having a human J chain component from a collection of human-nonhuman heterohybridoma clones capable of expressing human IgM type antibodies, the method comprising the steps of (a) collecting tissue culture fluid containing samples of IgM antibodies from each of the heterohybridomas, purifying the IgM antibodies, treating the antibodies under conditions sufficient to expose the J chain components of the antibodies;

(b) contacting separate portions of each J chain component with anti-human J chain antibodies and anti-nonhuman J chain antibodies capable of complexing with the nonhuman J chain components;

(c) determining which of the antibodies of step (b) complexes with the J chain components; and (d) selecting those heterohybridomas which produce IgM antibodies which bind to anti-human J chain antibodies.

6. The method of claim 5 wherein the heterohybridoma cells are mouse-human cells.

7. The method of claim 5 wherein a detergent is used to expose the J chain component in step (a).

8. The method of claim 7 wherein the exposure includes use of SDS.

9. A method of selecting a human-nonhuman heterohybridoma which expresses IgM antibodies having a human J chain component from a collection of human-nonhuman heterohybridoma clones capable of expressing human IgM type antibodies, the method comprising the steps of (a) collecting tissue culture fluid containing samples of IgM antibodies from each of the heterohybridomas and purifying the antibodies;

(b) subjecting the fluid to conditions sufficient to expose the J chain component of the IgM antibodies and reducing the antibodies into J chain, light chain and heavy chain components;

(c) contacting separate portions of each J chain component to anti-human J chain antibodies and anti-nonhuman J chain antibodies capable of complexing with the nonhuman J chain components;

(d) determining which of the antibodies of step (c) complexes with the J chain components; and (e) selecting those heterohybridomas which produce IgM antibodies which bind to anti-human J chain antibodies.

10. The method of claim 9 wherein the heterohybridoma cells are mouse-human cells.

11. The method of claim 9 wherein a detergent is used in step (b).

12. The method of claim 11 wherein the detergent is SDS.

13. The method of claim 9 wherein the reduction of step (b) is accomplished using a disulfide group reducing agent.

14. The method of claim 13 wherein the agent is $\beta$-mercaptoethanol.

* * * * *